United States Patent
Bartz et al.

(10) Patent No.: US 8,352,290 B2
(45) Date of Patent: Jan. 8, 2013

(54) METHOD OF AUTOMATICALLY PROGRAMMING AN INFUSION PUMP

(75) Inventors: Troy A. Bartz, Lake Orion, MI (US); Paul T Kotnik, Commerce Township, MI (US)

(73) Assignee: Curlin Medical Inc., East Aurora, NY (US)

( * ) Notice: Subject to any disclaimer, the term of this patent is extended or adjusted under 35 U.S.C. 154(b) by 0 days.

(21) Appl. No.: 13/127,499

(22) PCT Filed: Oct. 22, 2009

(86) PCT No.: PCT/US2009/061577
§ 371 (c)(1),
(2), (4) Date: Jul. 13, 2011

(87) PCT Pub. No.: WO2010/053702
PCT Pub. Date: May 14, 2010

(65) Prior Publication Data
US 2011/0259954 A1    Oct. 27, 2011

Related U.S. Application Data

(60) Provisional application No. 61/198,681, filed on Nov. 7, 2008.

(51) Int. Cl.
*G06Q 50/00* (2012.01)
*G06Q 10/00* (2012.01)
*G06F 17/00* (2006.01)

(52) U.S. Cl. .................................. 705/3; 705/2; 235/375

(58) Field of Classification Search .................. 235/375; 705/3, 2
See application file for complete search history.

(56) References Cited

U.S. PATENT DOCUMENTS

| | | |
|---|---|---|
| 2003/0197062 A1 | 10/2003 | Shaw |
| 2005/0144043 A1 | 6/2005 | Holland et al. |
| 2007/0233035 A1 | 10/2007 | Wehba et al. |

*Primary Examiner* — Thien M Le
*Assistant Examiner* — Toan Ly
(74) *Attorney, Agent, or Firm* — Hodgson Russ LLP

(57) ABSTRACT

A method of automatically programming an infusion pump includes scanning, via a machine-readable scanner wirelessly connected to the infusion pump, a machine-readable label for a drug container to automatically program the infusion pump according to a protocol included in the label. The machine-readable label for the drug container further includes a drug name and data associated with a drug corresponding to the drug name.

15 Claims, 1 Drawing Sheet

| | 100 |
|---|---|
| PROVIDING A MACHINE-READABLE LABEL FOR A DRUG CONTAINER, THE LABEL INCLUDING A DRUG NAME, DATA ASSOCIATED WITH A DRUG CORRESPONDING TO THE DRUG NAME, AND A PROTOCOL FOR INFUSING THE DRUG | |

↓

| | 102 |
|---|---|
| SCANNING THE LABEL, VIA A MACHINE-READABLE SCANNER, TO AUTOMATICALLY PROGRAM THE INFUSION PUMP ACCORDING TO THE PROTOCOL INCLUDED IN THE LABEL | |

METHOD OF AUTOMATICALLY PROGRAMMING AN INFUSION PUMP

CROSS REFERENCE TO RELATED APPLICATION

This application claims the benefit of U.S. Provisional Patent Application Ser. No. 61/198,681 for a METHOD OF AUTOMATICALLY PROGRAMMING AN INFUSION PUMP, filed on Nov. 7, 2008, which is hereby incorporated by reference in its entirety. This claim is made under 35 U.S.C. §119(e); 37 C.F.R. §1.78; and 65 Fed. Reg. 50093.

TECHNICAL FIELD OF INVENTION

The present disclosure relates generally to infusion pump systems, and more particularly to a method of automatically programming an infusion pump.

BACKGROUND

Infusion pumps are often used to deliver fluid in a controlled manner such as, for example, an intravenous delivery of pharmaceutical compositions (i.e., a drug) to a patient or subject. In many cases, the infusion pump is programmable with an infusion protocol for delivering the drug to the subject. The infusion protocol may be generated using a computer connected to the infusion pump via a wired connection. In such instances, the protocol is transferred from the computer to the infusion pump.

SUMMARY

A method of automatically programming an infusion pump is disclosed herein. The method includes scanning, via a machine-readable scanner wirelessly connected to the infusion pump, a machine-readable label for a drug container to automatically program the infusion pump according to a protocol included in the label. The machine-readable label for the drug container further includes a drug name and data associated with a drug corresponding to the drug name.

BRIEF DESCRIPTION OF THE DRAWINGS

Features and advantages of embodiment(s) of the present disclosure will become apparent by reference to the following detailed description and drawings, in which like reference numerals correspond to similar, though perhaps not identical components. Reference numerals having a previously described function may or may not be described in connection with other drawings in which they appear.

DETAILED DESCRIPTION

Figures 1, 2:
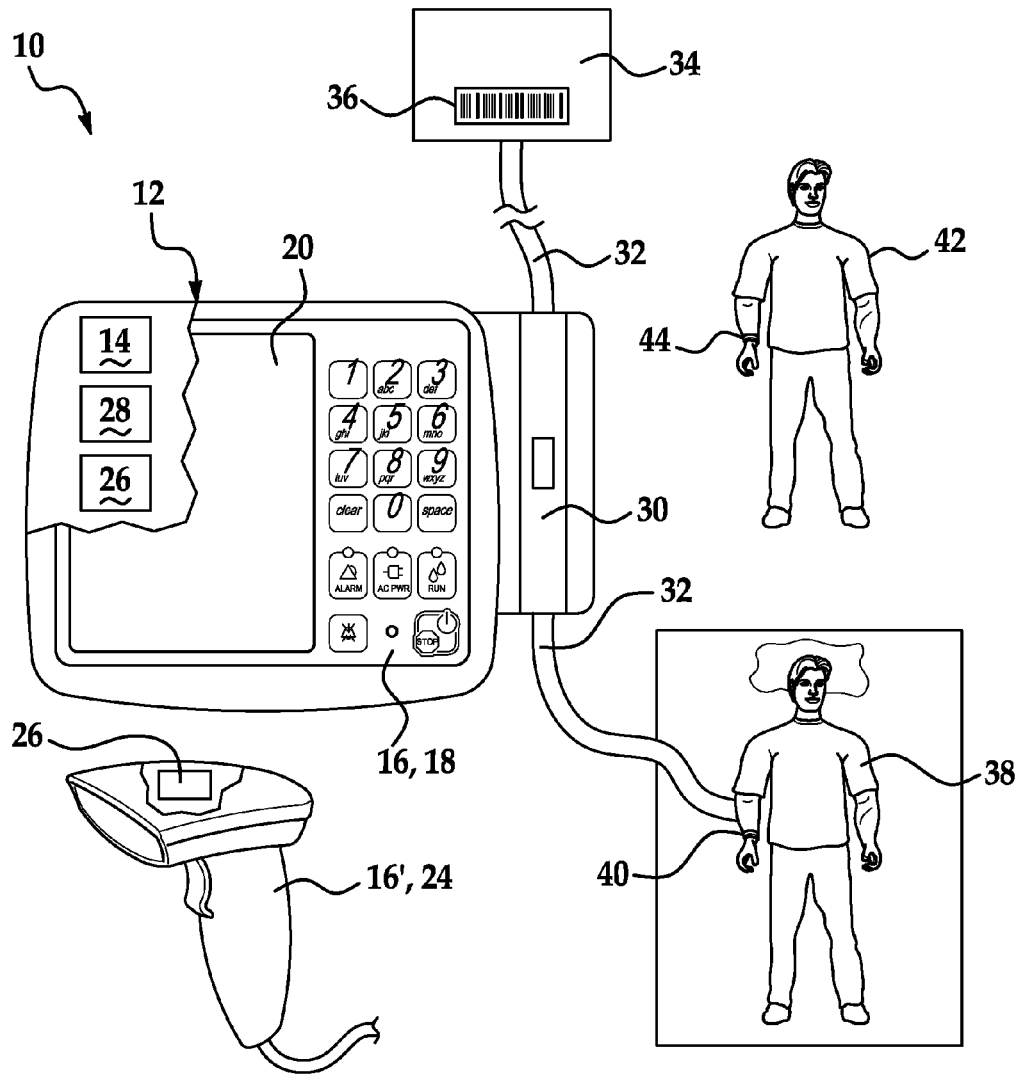
FIG. 1 is a semi-schematic depiction of an example of an infusion pump system.
FIG. 2 is a flow diagram schematically depicted an example of a method of automatically programming an infusion pump.

Embodiment(s) of the method as disclosed herein may advantageously be used to quickly, reliably, and automatically program an infusion pump. Such programming is accomplished by scanning, via a machine-readable scanner wirelessly connected to the infusion pump, at least a machine-readable label for a drug container. In some instances, the machine-readable scanner may also be used to read a machine-readable label for a subject and/or for a caregiver. In these instances, the subject and/or the caregiver may be located remote from the infusion pump. Thus, the wireless capability of the machine-readable scanner enables the scanner to be moved to areas remote from the infusion pump. This facilitates easier programming of the infusion pump, regardless of its location relative to the scanner.

The label includes, for example, the drug name, data associated with a drug corresponding to the drug name, and a protocol for infusing the drug to a subject. The machine-readable label is relatively easy to read by the scanner and, therefore, may be a popular alternative to manually entering the information into the infusion pump by hand. Further, scanning the machine-readable label may advantageously reduce errors that may occur when entering data into the infusion pump.

An example of an infusion pump system 10 that may be used for embodiment(s) of the method disclosed herein is semi-schematically depicted in FIG. 1. The infusion pump system 10 includes an infusion pump 12, such as a rotary peristaltic pump as shown in FIG. 1. Such rotary peristaltic infusion pumps may include a removable cassette 30 including an assembly of rollers (not shown) and a flexible tube 32 that surrounds a portion of the assembly of rollers. In response to rotational movement of the rollers, portions of the flexible tube 32 in contact with the rollers compress or otherwise occlude against a wall of the cassette 30. As a result, fluid (i.e., a drug) traveling through the tube 32, which was delivered from a drug container 34, is temporarily trapped in the tube 32 between the occluded points. The trapped drug is released from the tube 32 when the occlusion force on the tube 32 is released. In this manner, the drug is urged through the tube 32 via peristaltic wave action and is ultimately delivered to a subject 38.

While a rotary peristaltic pump is shown and described herein, it is to be understood that other infusion pumps are also suitable for use in the methods of the present disclosure. Examples of such other infusion pumps include syringe pumps and linear peristaltic pumps.

The infusion pump 12 also has associated therewith a memory 14 for storing a drug library including pre-established drug-related information for a plurality of drugs. Examples of pre-established drug-related information include, but are not limited to, drug names, appropriate concentration level(s) per dose of the drug, dose size(s), delivery rate information including minimum and/or maximum limits, and/or the like, and/or combinations thereof. Such information may be organized according to the drug and, in some instances, may further be organized according to a particular care area in a medical facility. Further details of the drug library may be found in U.S. Patent Provisional Application Ser. No. 61/198,683, which is herein incorporated by reference in its entirety.

Further, the infusion pump 12 includes a user interface 16 operatively connected thereto. In an embodiment, the user interface 16 is a twelve-digit keypad 18 operatively associated with a display screen 20. Together, the interface 16 and display screen 20 enable the manual entry of, e.g., drug-related data into the infusion pump 12. The display screen 20 may, in an example, be a standard display exhibiting black-and-white and/or color graphic and alpha-numeric characters. The display screen 20 may, in another example, be a color touch screen.

In some instances, the display screen 20 may further include an ambient light detection feature (not shown) to determine how optically bright the ambient environment is. The light detection feature may automatically adjust the backlighting of the display screen 20 depending on increased or decreased lighting of the ambient environment. Further, the display screen 20 may include a dimming feature, where the optical brightness of the display screen 20 dims when the infusion pump 12 is continuously operated at substantially the same setting(s).

Another embodiment of the user interface 16' (also shown in FIG. 1) is a machine-readable scanner 24 that wirelessly transmits information to the infusion pump 12 via a wireless connection established between the scanner 24 and the pump 12. The wireless connection may be enabled by appropriate hardware 26 provided in the infusion pump 12 and in the scanner 24. In an example, the machine-readable scanner is a barcode scanner configured to read barcode labels (as will be described in further detail below).

The infusion pump 12 further includes a processor 28 operatively connected thereto and in operative communication with the memory 14. The processor 26 is generally configured with one or more computer codes or algorithms for i) programming the infusion pump 12 according to the infusion protocol either manually entered (e.g., using the keypad 18) or wirelessly entered (e.g., using the barcode scanner 24), ii) running an infusion according to the infusion protocol, and/or iii) verifying accuracy of the subject's name, the drug name, the data associated with the drug, a caregiver's name, and/or the protocol for infusing the drug.

An example of a method of automatically programming the infusion pump 12 is schematically depicted in FIG. 2. With reference to FIGS. 1 and 2 together, in an embodiment, the method begins by providing a machine-readable label 36 for the drug container 34 (as shown by reference numeral 100). The machine-readable label 36 is, for example, a barcode label encoded with extensible markup language, binary code language, text, American standard code for information exchange, or combinations thereof. The barcode label 36 contains information therein, such information includes at least one of a drug name, data associated with a drug corresponding to the drug name, and a protocol for infusing the drug to a subject 38.

The method further includes scanning the label 36, via the machine-readable scanner 24, to automatically program the infusion pump 12 according the protocol included in the label (as shown by reference numeral 102 in FIG. 2). In an example, the barcode label 36 is placed or otherwise fixed to the drug container 34 either before or after the drug container 34 is connected to the flexible tube 32. To scan the barcode label 36, the barcode scanner 24, which is wirelessly connected to the infusion pump 12, may be moved to a location of the drug container 34. It is to be understood that, in some instances, the drug container 34 may be located proximate the infusion pump 12 and, in other instances, the drug container 34 may be located a distance from the infusion pump 12 (e.g., the drug container 34 may be located across the room from the infusion pump 12). The barcode scanner 24 reads the barcode label 36 and inputs, via the wireless connection with the pump 12, the data included in the barcode label 36 into the processor 28. The processor 28 uses the inputted data to program the infusion pump 12 for that particular infusion.

In an example, the processor 28 further includes at least one algorithm for verifying the drug-related information and/or the protocol for infusing the drug included in the barcode label 36 for the drug container 34. This is used at least as a safety measure to ensure that an amount of the drug, a concentration of the drug, a delivery method for infusing the drug, and/or the like are within approved safety standards. Verifying such information may be accomplished by comparing the drug name, the data associated with the drug, and the protocol for infusing the drug with the pre-established drug-related information saved in the drug library (described above).

With reference again to FIG. 1, in another embodiment, the barcode label 36 further includes a name of the subject 38 intended to receive the drug. The subject 38 may be, for example, a person, an animal, or other living organism capable of receiving the drug. In this embodiment, the method further includes providing a machine-readable label 40 for the subject 38 (e.g., a barcode label similar to the barcode label 36 for the drug container 34) that includes at least the subject's name and personal information associated with the subject 38. Non-limiting examples of personal information include the subject's weight, the subject's height, any allergies that the subject 38 may have, and/or the like.

Either before or after the barcode scanner 24 scans the barcode label 36 of the drug container 34, the barcode scanner 24 is also used to scan the barcode label 40 worn by the subject 38. The scanned information is inputted into the processor 28 of the infusion pump 12, where the processor 28 uses a computer algorithm to verify that the subject 38 is in fact the intended recipient of the drug contained in the drug container 34. The algorithm enables a comparison of the subject's name included in the barcode label 40 for the subject 38 with the name of the subject included in the barcode label 36 for the drug container 34. If a match exists between the two names, the infusion pump 12 is automatically programmed according to the protocol included in the barcode label 36 for the drug container 34. At this point, a process for infusing the drug to the subject 38 may begin.

In the event that the subject's name included in the barcode label 40 for the subject 38 does not match the subject's name included in the barcode label 36 for the drug container 38, the protocol for infusing the drug is rejected by the infusion pump 12. In this case, the infusion pump 12 may indicate an error on the display screen 20 or sound an alarm alerting a caregiver or other person proximate the pump that an error has occurred. In some instances, an error report may be sent to a remotely located central station (e.g., a nurse's station for the care area that the subject 38 is currently located in).

In yet another embodiment, the method further includes providing a machine-readable label 44 for the caregiver 42 (e.g., a barcode label similar to the barcode label 36 for the drug container 34 and the barcode label 40 for the subject 38) that includes the caregiver's name and, in some instances, other information related to the identity of the caregiver 42. The caregiver's information may be stored by the pump 12 to produce a record of the identity of the person that administered the drug to the subject 38. In this embodiment, the barcode scanner 24 is used to scan the barcode label 44 of the caregiver 42 and then scan the barcode label 40 of the subject 38 and the barcode label 36 of the drug container 34. It is to be understood that the scanning order provided above is not fixed and that any order of scanning may be used to input the information into the infusion pump 12.

In still another embodiment, rather than using a barcode label 40, 44 for inputting, into the infusion pump 12, information related to the subject 38 and/or information related to the caregiver 42, the method includes manually inputting at least the subject's name and/or the caregiver's name using the keypad 18. In instances where the subject's name is manually input, the manually inputted information related to the subject 38 is compared with that included in the barcode label 36 for the drug container 34 and, if a match exists, the infusion pump 12 is automatically programmed according to the protocol included in the barcode label 36.

The infusion pump system 10 as described above is configured such that information related to the drug, the protocol for infusing the drug, the subject 38, and the caregiver 42 may be inputted via a barcode scan. It is to be understood, however, that the infusion pump system 10 is also configured to allow any or all of the foregoing pieces of information to be input manually. It is also to be understood that the embodiments provided above do not provide an exhaustive list of all possible configurations of programming the infusion pump 10, and, thus other possible configurations are also contemplated although may not be explicitly stated or described herein.

It is further to be understood that the term "connect/connected" or the like is broadly defined herein to encompass a variety of divergent connection arrangements and assembly techniques. These arrangements and techniques include, but are not limited to 1) the direct connection between one component and another component with no intervening components therebetween; and 2) the connection of one component and another component with one or more components therebetween, provided that the one component being "connected to" the other component is somehow operatively connected to the other component (notwithstanding the presence of one or more additional components therebetween).

While several embodiments have been described in detail, it will be apparent to those skilled in the art that the disclosed embodiments may be modified. Therefore, the foregoing description is to be considered exemplary rather than limiting.

What is claimed is:

1. A method of automatically programming an infusion pump, the method comprising:
    providing a machine-readable label for a drug container, the machine-readable label for the drug container including a drug name, data associated with a drug corresponding to the drug name, and a protocol for infusing the drug; and
    scanning the label, via a machine-readable scanner wirelessly connected to the infusion pump, to automatically program the infusion pump according to the protocol included in the label and patient information for each particular infusion.

2. The method as defined in claim 1 wherein the machine-readable label for the drug container is a bar code label, and wherein the machine-readable scanner is a bar code scanner.

3. The method as defined in claim 2 wherein the bar code label is encoded with extensible markup language, binary code language, text, American standard code for information interchange, or combinations thereof.

4. The method as defined in claim 1 wherein the machine-readable label for the drug container further includes a name of a subject, and wherein the method further comprises:
    providing a machine-readable label for the subject, the machine-readable label for the subject including at least the subject's name and personal information associated with the subject;
    scanning the machine-readable label of the subject via the machine-readable scanner;
    comparing the subject's name included in the machine-readable label for the subject with the name of the subject included in the machine-readable label for the drug container; and
    determining whether a match exists between the subject's name included in the machine-readable label for the subject and the name of the subject included in the machine-readable label for the drug container.

5. The method as defined in claim 4 wherein a match exists between the subject's name included in the machine-readable label for the subject and the name of the subject included in the machine-readable label for the drug container, and wherein the method further comprises automatically programming the infusion pump with the protocol included in the machine-readable label for the drug container.

6. The method as defined in claim 4 wherein a match does not exist between the subject's name included in the machine-readable label for the subject and the name of the subject included in the machine-readable label for the drug container, and wherein the method further comprises rejecting the protocol for infusing the drug.

7. The method as defined in claim 4 wherein the machine-readable label for the subject is a bar code label encoded with extensible markup language.

8. The method as defined in claim 1 wherein prior to automatically programming the infusion pump, the method further comprises verifying that the drug name, the data associated with the drug name, and the protocol for infusing the drug are accurate.

9. The method as defined in claim 8 wherein verifying is accomplished by comparing the drug name, the data associated with the drug name, and the protocol for infusing the drug with pre-established drug-related information saved in a drug library that is stored in the infusion pump.

10. The method as defined in claim 1, further comprising:
    providing a machine-readable label for a caregiver, the machine-readable label including at least the caregiver's name; and
    scanning the machine-readable label for the caregiver via the machine-readable scanner.

11. A method of automatically programming an infusion pump, the method comprising:
    providing a machine-readable label for a drug container, the machine-readable label for the drug container including a drug name, data associated with a drug corresponding to the drug name, and a protocol for infusing the drug; and
    scanning the label, via a machine-readable scanner wirelessly connected to the infusion pump, to automatically program the infusion pump according to the protocol included in the label:
    wherein the machine-readable label for the drug container further includes a name of a subject, and wherein the method further comprises:
    manually inputting at least a name corresponding with the subject into the infusion pump via a user interface on the infusion pump;
    comparing, via a controller in the infusion pump, the subject's name manually inputted into the infusion pump with the name of the subject included in the machine-readable label for the drug container;
    determining that a match exists between the subject's name manually inputted into the infusion pump and the name of the subject included in the machine-readable label for the drug container; and
    automatically programming the infusion pump with the protocol included in the machine-readable label for the drug container.

12. An infusion pump system, comprising:
    an infusion pump having stored therein a drug library including pre-established drug-related information for a plurality of drugs;
    a user interface on the infusion pump configured to receive, via: a manual input; a wireless input; or a combination thereof, a subject's name, a caregiver's name, a drug name, data associated with a drug corresponding to the drug name, and a protocol for infusing the drug; and a processor in the infusion pump and configured with at least one computer code for verifying accuracy of the protocol for infusing the drug for each particular infusion and for verifying at least one of the subject's name, the caregiver's name, the drug name, the data associated with the drug.

13. The infusion pump system as defined in claim 12 wherein the user interface includes a twelve-digit keypad associated with a display screen.

14. The infusion pump system as defined in claim 13 wherein the display screen is a color touch screen.

15. The infusion pump system as defined in claim 12 wherein the user interface is a wireless barcode scanner configured to read barcode labels encoded with extensible markup language, binary code language, text, American standard code for information interchange, or combinations thereof.

* * * * *

(12) EX PARTE REEXAMINATION CERTIFICATE (10898th)
United States Patent
Bartz et al.

(10) Number: US 8,352,290 C1
(45) Certificate Issued: Jun. 24, 2016

(54) METHOD OF AUTOMATICALLY PROGRAMMING AN INFUSION PUMP

(75) Inventors: Troy A. Bartz, Lake Orion, MI (US); Paul T Kotnik, Commerce Township, MI (US)

(73) Assignee: CURLIN MEDICAL INC., East Aurora, NY (US)

Reexamination Request:
No. 90/013,628, Nov. 13, 2015

Reexamination Certificate for:
| | |
|---|---|
| Patent No.: | 8,352,290 |
| Issued: | Jan. 8, 2013 |
| Appl. No.: | 13/127,499 |
| PCT Filed: | Oct. 22, 2009 |
| PCT No.: | PCT/US2009/061577 |
| § 371 (c)(1), (2), (4) Date: | Jul. 13, 2011 |
| PCT Pub. No.: | WO2010/053702 |
| PCT Pub. Date: | May 14, 2010 |

Related U.S. Application Data

(60) Provisional application No. 61/198,681, filed on Nov. 7, 2008.

(51) Int. Cl.
| | |
|---|---|
| *G06Q 50/00* | (2012.01) |
| *G06Q 10/00* | (2012.01) |
| *G06F 17/00* | (2006.01) |
| *A61M 5/145* | (2006.01) |
| *G06F 19/00* | (2011.01) |
| *A61M 5/142* | (2006.01) |

(52) U.S. Cl.
CPC ........... *A61M 5/145* (2013.01); *A61M 5/14212* (2013.01); *G06F 19/3468* (2013.01); *A61M 5/1452* (2013.01); *A61M 5/14228* (2013.01); *A61M 5/14232* (2013.01); *A61M 2205/3561* (2013.01); *A61M 2205/3592* (2013.01); *A61M 2205/6009* (2013.01); *A61M 2205/6018* (2013.01); *A61M 2205/6072* (2013.01); *G06F 19/326* (2013.01)

(58) Field of Classification Search
None
See application file for complete search history.

(56) References Cited

To view the complete listing of prior art documents cited during the proceeding for Reexamination Control Number 90/013,628, please refer to the USPTO's public Patent Application Information Retrieval (PAIR) system under the Display References tab.

*Primary Examiner* — Kenneth J Whittington

(57) ABSTRACT

A method of automatically programming an infusion pump includes scanning, via a machine-readable scanner wirelessly connected to the infusion pump, a machine-readable label for a drug container to automatically program the infusion pump according to a protocol included in the label. The machine-readable label for the drug container further includes a drug name and data associated with a drug corresponding to the drug name.

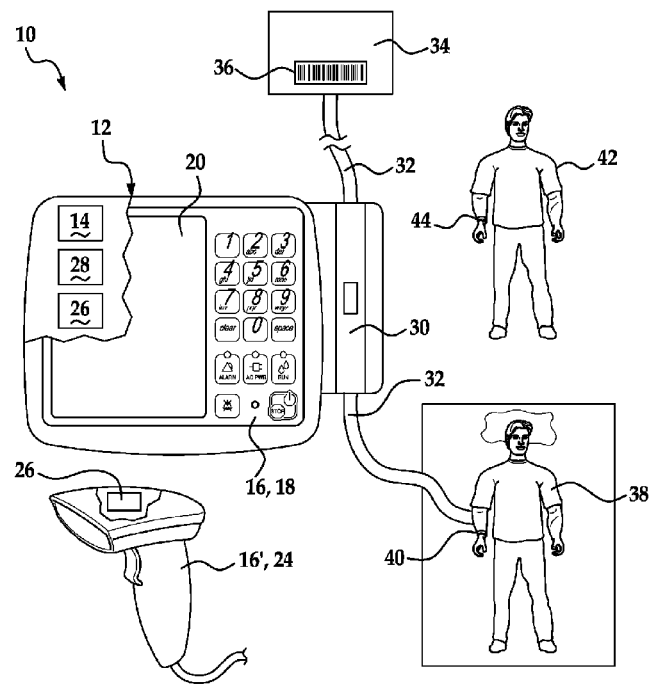

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-15 are cancelled.

* * * * *